(12) United States Patent
Abe et al.

(10) Patent No.: US 8,168,227 B2
(45) Date of Patent: May 1, 2012

(54) MODIFIED POWDER AND COSMETIC COMPOSITION USING THE SAME

(75) Inventors: Koji Abe, Yokohama (JP); Hidefumi Araki, Yokohama (JP); Shuji Nishihama, Yokohama (JP); Tetsuya Kanemaru, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 909 days.

(21) Appl. No.: 11/721,472

(22) PCT Filed: Dec. 13, 2005

(86) PCT No.: PCT/JP2005/022900
§ 371 (c)(1),
(2), (4) Date: Jun. 14, 2007

(87) PCT Pub. No.: WO2006/064821
PCT Pub. Date: Jun. 22, 2006

(65) Prior Publication Data
US 2007/0253989 A1    Nov. 1, 2007

(51) Int. Cl.
*A61K 9/14* (2006.01)
*A61K 8/19* (2006.01)

(52) U.S. Cl. .......... 424/490; 424/489; 424/401; 424/63; 424/69

(58) Field of Classification Search .................. 424/490, 424/401, 489, 63, 69
See application file for complete search history.

(56) References Cited

U.S. PATENT DOCUMENTS

| | | | |
|---|---|---|---|
| 5,744,126 A | 4/1998 | Horino et al. | |
| 6,482,441 B1 * | 11/2002 | Hasegawa et al. | 424/490 |
| 2004/0091440 A1 | 5/2004 | Kamei et al. | |
| 2004/0241126 A1 * | 12/2004 | Sakuta | 424/70.12 |
| 2005/0118121 A1 * | 6/2005 | Kuroda | 424/63 |

FOREIGN PATENT DOCUMENTS

| | | |
|---|---|---|
| JP | 2001-220338 | 8/2001 |
| JP | 2001-335410 A * | 12/2001 |
| JP | 2001335410 A | 12/2001 |

OTHER PUBLICATIONS

Sagara, K. et al. "Powder Cosmetic", JP 2001335410 A, Dec. 4, 2001, abstract.*
Sagara, K. et al. JP 2001-335410 A, Dec. 4, 2001, machine translation, printed on May 25, 2010.*
Japanese Patent Abstract Publication No. 08-059448 published Mar. 5, 1996, one page.
Japanese Patent Abstract Publication No. 08-208425 published Aug. 13, 1996, one page.
Patent Abstract of Japan: 2001-220338, published Aug. 14, 2001, Applicant—Shiseido Co Ltd., nine pages.
European Search Report dated Apr. 8, 2011; Application No./Patent No. 05816803.0-2108 / 1832272 PCT/JP2005022900, 6 pages.
Japanese Patent Abstract Publication No. 2001335410 published Dec. 4, 2001, 1 page.
International Search Report for PCT/JP2005/022900 mailed Apr. 4, 2006, two pages.
Japanese Patent Abstract Publication No. 2002-173611, published Jun. 21, 2002, one page.
Japanese Patent Abstract Publication No. 2004-010735, published Jan. 15, 2004, one page.
Japanese Patent Abstract Publication No. 2004-189652, published Jul. 8, 2004, one page.

* cited by examiner

*Primary Examiner* — Gina C Yu
(74) *Attorney, Agent, or Firm* — Rankin, Hill & Clark LLP (57) ABSTRACT

The present invention provides a modified powder that is obtainable by coating the surface of a base powder with a hydrophobizing agent and a cationic surfactant. In the modified powder described above, it is preferable that the amount of coated hydrophobizing agent and the amount of coated cationic surfactant are 3 to 90% by mass and 0.5 to 10% by mass, respectively, relative to the self weight of the base powder. In the modified powder described above, it is preferable that the mass ratio of the coated hydrophobizing agent and the coated cationic surfactant is from 1:1 to 9:1. In addition, the present invention provides a cosmetic composition comprising the above modified powder wherein the modified powder and the base powder have an ultraviolet scattering effect. In the cosmetic composition described above, it is preferable that the blended amount of the modified powder is from 0.5 to 100% by mass. Furthermore, the present invention provides a sunscreen cosmetic composition comprising the above modified powder with an ultraviolet scattering effect. In the sunscreen cosmetic composition described above, it is preferable that the base powder is one or more selected from the group consisting of titanium oxide, zinc oxide, iron oxide, cerium oxide, bismuth oxide, zirconium oxide, chromium oxide, and tungstic acid. In the sunscreen cosmetic composition described above, it is preferable that the blended amount of the modified powder is from 1 to 40% by mass.

19 Claims, 1 Drawing Sheet

MODIFIED POWDER AND COSMETIC COMPOSITION USING THE SAME

RELATED APPLICATIONS

This application claims from priority Japanese Patent Application No. 2004-360124 filed on Dec. 13, 2004 and Japanese Patent Application No. 2004-360125 filed on Dec. 13, 2004 which are incorporated herein by reference.

BACKGROUND OF THE INVENTION

1. Field of the Invention

The present invention relates to a modified powder excellent in water resistance, cleansability, and ultraviolet protection effect and to a cosmetic composition using the same, and in particular, relates to a sunscreen cosmetic composition containing an inorganic ultraviolet scattering agent.

2. Prior Art

In the past, the functions such as coloring the skin, hiding pigmented spots and freckles, and protecting the skin from ultraviolet light were provided by blending powder into cosmetic compositions. In recent years, in order to achieve longer-lasting makeup, powders, the surface of which is hydrophobized, are frequently used (refer to Japanese Unexamined Patent Publication H08-208425 and Japanese Unexamined Patent Publication H08-059448).

Middle wavelength ultraviolet light (290-320 nm) in the sunlight is known to cause the formation of erythema and blisters, an increase in melanogenesis, pigmentation, etc.

In addition, long wavelength ultraviolet light (320-400 nm) has an immediate pigment darkening effect, which darkens the skin immediately after exposure. Its energy reaches the dermis; therefore, the vascular wall and the elastic fibers of the connective tissue are also affected. The effect of the middle to long wavelength ultraviolet light promotes the aging of the skin, and it is considered to be part of the reason for pigmented spots, freckles, wrinkles, and skin cancer.

In order to protect the skin from ultraviolet light, titanium dioxide powder, zinc oxide powder, etc. have been used as ultraviolet scattering agents. In recent years, in order to increase water resistance, ultraviolet scattering agents, the surface of which is hydrophobized, are frequently used.

For example, sunscreen cosmetic compositions containing fine titanium dioxide particles, the surface of which is treated with metallic soap, are publicly known (refer to Japanese Unexamined Patent Publication H08-208425).

However, the cosmetic compositions containing a powder, the surface of which is hydrophobized, often remains on the skin, after cleansing, because the makeup is long-lasting.

In particular, it is difficult to remove, with a normal cleanser, sunscreen cosmetic compositions that contain, as an ultraviolet scattering agent, a powder, the surface of which is hydrophobized. This is because of the good water resistance of the cosmetic compositions, and it is recommended to use a special cleanser. As a result, such sunscreen cosmetic compositions sometimes gave consumers an impression that they are unsuitable for everyday use.

The objects of the present invention are to provide new powders with excellent water resistance, easy removal with a normal cleanser, and the ultraviolet protection effect, to provide cosmetic compositions containing the new powder, and in particular to provide sunscreen cosmetic compositions containing an ultraviolet scattering agent.

SUMMARY OF THE INVENTION

The present inventors have diligently researched in view of the above-described problem. As a result, the present inventors have found that a powder with both water resistance and cleansability could be obtained by coating the powder surface with a hydrophobizing agent and a cationic surfactant and that the ultraviolet protection effect of cosmetic compositions could also be improved.

Thus, the present invention provides a modified powder that is obtainable by coating the surface of a base powder with a hydrophobizing agent and a cationic surfactant.

In the modified powder described above, it is preferable that the amount of coated hydrophobizing agent and the amount of coated cationic surfactant are 3 to 90% by mass and 0.5 to 10% by mass, respectively, relative to the self weight of the base powder.

In the modified powder described above, it is also preferable that the mass ratio of the coated hydrophobizing agent and the coated cationic surfactant is from 1:1 to 9:1.

The present inventors found that a cosmetic composition with both water resistance and cleansability and with a high ultraviolet protection effect could be obtained by blending the above-described modified powder or an ultraviolet scattering agent contained in the modified powder.

Thus, the cosmetic composition of the present invention prefers to comprise the above modified powder with an ultraviolet scattering effect.

In addition, the cosmetic composition of the present invention are characterized by comprising the above modified powder.

In the cosmetic composition described above, it is also preferable that the blended amount of the modified powder is from 0.5 to 100% by mass.

The present inventors also found that a sunscreen cosmetic composition with both water resistance and cleansability and with a high ultraviolet protection effect could be obtained by blending an ultraviolet scattering agent contained in the modified powder.

Thus, the sunscreen cosmetic composition of the present invention is characterized in that the base powder of the above modified powder has an ultraviolet scattering effect.

In the sunscreen cosmetic composition described above, it is preferable that the base powder with an ultraviolet scattering effect is one or more selected from the group consisting of titanium oxide, zinc oxide, iron oxide, cerium oxide, bismuth oxide, zirconium oxide, chromium oxide, and tungstic acid.

In the sunscreen cosmetic composition described above, it is also preferable that the blended amount of the modified powder is from 1 to 40% by mass.

The modified powder, of the present invention, with excellent water resistance and cleansability can be obtained by coating the surface of a base powder with a hydrophobizing agent and a cationic surfactant.

In addition, a cosmetic composition with both water resistance and cleansability can be obtained by blending such a modified powder.

In particular, a sunscreen cosmetic composition with good water resistance and easy removal with a normal cleanser can be obtained by using such a modified powder as an ultraviolet scattering agent.

The modified powder and cosmetic composition of the present invention are also excellent in the ultraviolet protection effect.

DESCRIPTION OF THE PREFERRED EMBODIMENT

In the following, the mode for carrying out the present invention is described in detail.

The present invention is characterized in that the base powder is coated with a hydrophobizing agent and a cationic surfactant.

In the following section, base powders, hydrophobizing agents, and cationic surfactants, which can be used in the present invention, will be described in detail.

<Base Powder>

In the present invention, the base powder to be modified is not limited in particular, and any shape such as a sphere, plate, or needle; any particle size such as an aerosol size, fine particle, or pigment size; and any particle structure such as a porous or nonporous structure can be used so far as it is a powder commonly used in cosmetics. Specific examples include inorganic powders such as titanium oxide, black titanium oxide, Prussian blue, ultramarine, red iron oxide, yellow iron oxide, black iron oxide, zinc oxide, aluminum oxide, silicon dioxide, magnesium oxide, zirconium oxide, magnesium carbonate, calcium carbonate, chromium oxide, chromium hydroxide, carbon black, aluminum silicate, magnesium silicate, magnesium aluminum silicate, mica, synthetic mica, synthetic sericite, sericite, talc, kaolin, silicon carbide, barium sulfate, bentonite, smectite, and boron nitride; brilliant powders such as bismuth oxychloride, titanated mica, iron oxide coated mica, iron oxide-coated titanated mica, organic pigment-treated titanated mica, and aluminum powder; organic powders such as nylon powder, polymethyl methacrylate powder, acrylonitrile-methacrylic acid copolymer powder, vinylidene chloride-methacrylic acid copolymer powder, polyethylene powder, polystyrene powder, organopolysiloxane elastomer powder, polymethylsilsesquioxane powder, wool powder, silk powder, crystalline cellulose, and N-acyllysine; pigment powders such as organic tar pigment and organic lake pigment; and composite powders such as fine titanium oxide particle-coated titanated mica, fine zinc oxide particle-coated titanated mica, barium sulfate-coated titanated mica, silicon dioxide-containing titanium oxide, and silicon dioxide-containing zinc oxide. One kind or more than one kind of these can be used.

The base powder used in the cosmetic composition of the present invention, especially the base powder used in a sunscreen cosmetic composition is not limited in particular, and any shape such as a sphere, plate, or needle; any particle size such as an aerosol size, fine particle, or pigment size; and any particle structure such as a porous or nonporous structure can be used so far as it has an ultraviolet scattering effect and is a powder commonly used in cosmetics.

Specific examples include titanium oxide, zinc oxide, iron oxide, cerium oxide, bismuth oxide, zirconium oxide, chromium oxide, and tungstic acid. One kind or more than one kind of these can be used. Among these, titanium oxide and zinc oxide are preferable.

<Hydrophobizing Agents>

The hydrophobizing agent is not limited in particular, and any publicly known hydrophobizing agent can be used. Specific examples include silicone compounds such as dimethylpolysiloxane, methylhydrogenpolysiloxane, and methylphenylpolysiloxane; fluorine compounds such as perfluoroalkyl group-containing esters, perfluoropolyethers, and perfluoroalkyl group-containing polymers; oils and fats such as liquid paraffin, squalane, Vaseline, lanolin, microcrystalline wax, and polyethylene wax; metallic soaps such as aluminum laurate and aluminum stearate; organic titanates such as isopropyltriisostearoyl titanate; and silane coupling agents such as perfluoroalkyl silane and octyltriethoxysilane. One kind or more than one kind of these can be used.

<Cationic Surfactants>

Examples of cationic surfactants include stearyltrimethylammonium chloride, hexadecyltrimethylammonium chloride, tetradecyltrimethylammonium chloride, lauryltrimethylammonium chloride, C12 monohydroxyalkylether cation, dihydroxyalkylether cation, cocodiamidopropyl cation, cocodicarboxyethyl cation, C16 dicarboxyethyl cation, C18 dicarboxyethyl cation, POP(15) diethylmethyl cation, POP(25) diethylmethyl cation, POP(40) diethylmethyl cation, C12 diamidopropylmethylamine, C14 diamidopropylmethylamine, C16 diamidopropylmethylamine, C18 diamidopropylmethylamine, iso C18 diamidopropylmethylamine, di C18 propyldimethyl cation, hydroxypropyl-bis-lauryl cation, hydroxypropyl-bis-stearyl cation, hydroxypropyl-bis-laurylamide cation, hydroxypropyl-bis-stearylamide cation, C18 monohydroxyalkylether cation, bis-C18 hydroxyalkylether cation, C22 trimethylammonium bromide, C22 propyldimethylamine, quaternium-91, C22 trimethylammonium methosulfate, dicocoylamidoethylethylhydroxy cation, di C18 amidoethylethylhydroxy cation, di C16 amidoethylethylhydroxy cation, di C18 dimethylammonium salt, C18 dimethylbenzylammonium salt, perfluorotrimethylammonium salt, and diacylamidoethylethylhydroxy cation. One kind or more than one kind of these can be used.

A preferable cationic surfactant is distearyldimethylammonium salt, dihexadecyldimethylammonium salt, ditetradecyldimethylammonium salt, didodecyldimethylammonium salt, stearyltrimethylammonium chloride, hexadecyltrimethylammonium chloride, tetradecyltrimethylammonium chloride, or dodecyltrimethylammonium chloride. In particular, a dialkyl type is preferable from a view point of the balance in water resistance and cleansability of the powder.

In the present invention, the amount of coated hydrophobizing agent and the amount of coated cationic surfactant are preferably 3 to 90% by mass and 0.5 to 10% by mass, respectively, relative to the self weight of the base powder.

In addition, the mass ratio of the coated hydrophobizing agent and the coated cationic surfactant is preferably from 1:1 to 9:1. If the percentage of the cationic surfactant is higher than the above-described range, the water resistance may become worse. If the percentage of the cationic surfactant is lower than the above-described range, the cleansability may become worse.

In the following section, the preparation methods of the present invention are described in detail.

As the preparation method of the modified powder of the present invention, the following methods are described as examples; however, the present invention is not limited by these examples.

Into the solvent, 3 to 90% by mass, relative to the powder, of each hydrophobizing agent and 0.5 to 10% by mass, relative to the powder, of each cationic surfactant are added and dissolved. Then, the base powder is added to the solution, and the mixture is stirred for 1 hour at room temperature. After the stirring is completed, the desired modified powder was obtained by solvent removal, drying, and powdering.

As the solvent, methyl alcohol, ethyl alcohol, isopropyl alcohol, etc. that can dissolve various hydrophobizing agents and cationic surfactants can be used; in particular, isopropyl alcohol is preferable.

The modified powder of the present invention can also be prepared by treating a commercial hydrophobized powder with a cationic surfactant.

Examples of usable hydrophobized powders include metallic soap-treated powder (titanium oxide MT-100TV™ etc.) obtained by treatment with aluminum stearate etc., fatty acid-dextrin treated powder (WSX-Transparon™ etc.) obtained by treatment with cyclodextrin-fatty acid ester etc., amino acid treated powder (LL5-ST(HS)™ etc.) obtained by treatment with N-lauroyl-L-lysine etc., silicone treated powder (SS-Activox80™ etc.) obtained by treatment with methylhydrogenpolysiloxane, methylhydrogenpolysiloxane-dimethylpolysiloxane copolymer, dimethylpolysiloxane, and silica+dimethylpolysiloxane etc., fluorine-treated powder (PF™ etc.) obtained by treatment with perfluoroalkyl phosphate etc., and silane coupling agent treated powder (OTS™ etc.) obtained by treatment with octyltriethoxysilane etc. Among these, examples of preferable powders include silane coupling agent treated powder etc (OTS™ etc.) obtained by treatment with octyltriethoxysilane etc.

The amount of a modified powder blended in the cosmetic composition of the present invention is preferably 0.5 to 100% by mass of the composition.

In the cosmetic composition of the present invention, in addition to the above-described modified powders, water, oil, powder (untreated), surfactant, fluorine compounds, resins, thickener, preservative, perfume, ultraviolet light absorber, moisturizer, bioactive components, salts, solvent, antioxidant, chelating agent, neutralizing agent, pH adjuster, etc., which are normally used in cosmetics, can be blended so far as the effect of the present invention is not undermined.

The forms of cosmetic composition of the present invention are not limited in particular. Their examples include makeup cosmetic compositions such as foundation, white face powder, lipstick, eye shadow, cheek color, mascara, and eye liner; pre-makeup cream; and hair cream.

The amount of a modified powder blended in a sunscreen cosmetic composition of the present invention is preferably 1 to 40% by mass of the composition. If the amount of the blended powder is less than 1% by mass, the ultraviolet protection effect may not be achieved. If the amount of the blended powder is over 40% by mass, it is not desirable in the product formulation.

It is also desirable that the sunscreen cosmetic composition of the present invention contains an organic ultraviolet light absorber.

Examples of ultraviolet light absorbers include benzoic acid family ultraviolet light absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc.); anthranilic acid family ultraviolet light absorbers (for example, homomethyl N-acetylanthranilate etc.); salicylic acid family ultraviolet light absorbers (for example, amyl salicylate, menthyl salicylate, homomethyl salicylate, octyl salicylate, phenyl salicylate, benzyl salicylate, p-isopropanolphenyl salicylate, etc.); cinnamic acid family ultraviolet light absorbers (for example, octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, etc.); benzophenone family ultraviolet light absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc.); 3-(4'-methylbenzylidene)-d,l-camphor and 3-benzylidene-d,l-camphor; 2-phenyl-5-methylbenzoxazol; 2,2'-hydroxy-5-methylphenylbenzotriazol, 2-(2'-hydroxy-5'-t-octylphenyl)benzotriazol, and 2-(2'-hydroxy-5'-methylphenylbenzotriazol; dibenzalazine; dianisoylmethane; 4-methoxy-4'-t-butyldibenzoylmethane; and 5-(3,3-dimethyl-2-norbornylidene)-3-pentane-2-one and dimorpholinopyridazinone.

In the sunscreen cosmetic composition of the present invention, in addition to the above-described components, other components normally used in skin external preparations such as cosmetics and pharmaceuticals can be blended, as necessary, so far as the effect of the present invention is not undermined. Examples include other powder components, liquid fat, solid fat, wax, hydrocarbons, higher fatty acids, higher alcohols, esters, silicones, anionic surfactants, cationic surfactants, amphoteric surfactants, nonionic surfactants, moisturizer, water-soluble polymers, thickener, film-forming agents, metal ion sequestering agents, lower alcohols, polyhydric alcohols, saccharides, amino acids, organic amines, polymer emulsion, pH adjuster, skin nutrients, vitamins, antioxidants, antioxidant promoters, perfume, and water. The cosmetic composition can be prepared by ordinary methods according to the desired form.

The present invention will hereinafter be described in further detail by examples, but the present invention is not limited by these examples. The blended amount is expressed in % by mass, unless otherwise noted, relative to the system to which the component is blended.

EXAMPLE 1

The test methods of the present invention will be described at first.

<Cleansability Test Method>

On the inner side of the forearm (area of 10 cm×5 cm) is applied 0.1 mL of the sample (2 μL/cm2). The area is dried for 15 minutes, and the sample on the applied section (area of 2 cm diameter) is extracted with 5 mL of acetone (before cleansing). Then 2 mL of commercial body soap is sufficiently foamed, and the sample-applied section is cleansed by rubbing five times with the soap. The sample-applied section is rinsed with water and dried, and the sample of the applied section (another area of 2 cm diameter) is extracted with 5 mL of acetone (after cleansing).

The acetone solutions before and after the cleansing are analyzed with an ICP (inductively coupled plasma mass spectrometer) to determine the content of the inorganic powder. Thus, how much inorganic powder is left in the acetone solution after cleansing is determined by comparing with the acetone solution before cleansing.

A: The residual amount is less than 20%.

B: The residual amount is equal to or more than 20% and less than 30%.

C: The residual amount is equal to or more than 30% and less than 40%.

D: The residual amount is equal to or more than 40%.

<Water Resistance Test Method>

On the inner side of the forearm (area of 10 cm×5 cm) is applied 0.1 mL of the sample (2 µL/cm2), and the area is dried for 15 minutes.

The sample on the applied section (area of 2 cm diameter) is extracted with 5 mL of acetone (before cleansing).

The inner side of the forearm is exposed to flowing water for 15 minutes, and the sample of the applied section (another area of 2 cm diameter) is extracted with 5 mL of acetone (after cleansing).

The absorbances at 325 nm of the acetone solutions before and after the cleansing are compared, and how much inorganic powder is left in the acetone solution after cleansing is determined by comparing with the acetone solution before cleansing.

The evaluation criteria are as follows.
A: Equal to or more than 85% of the sample is left.
B: Equal to or more than 75% and less than 85% of the sample is left.
C: Equal to or more than 65% and less than 75% of the sample is left.
D: Less than 65% of the sample is left.

<Ultraviolet Protection Effect>

We requested 20 professional panelists to use the sample on a sunny day to evaluate the ultraviolet protection effect (2 µL/cm$^2$ of the sample is applied on the inner side of the forearm, and the area is dried for 15 minutes).

The evaluation criteria are as follows.
A: More than 15 out of 20 panelists answer that the ultraviolet protection effect is good.
B: From 12 to 15 out of 20 panelists answer that the ultraviolet protection effect is good.
C: From 6 to 11 out of 20 panelists answer that the ultraviolet protection effect is good.
D: Less than 6 out of 20 panelists answer that the ultraviolet protection effect is good.

In the following section, preparation methods of the powders used in the testing are described.

TEST EXAMPLE 1

Silane Coupling Agent Treatment+Cation Treatment

To 200 mL of isopropyl alcohol were added 6 g of octyltriethoxysilane and 2 g of diC18dimethylammonium salt and they were dissolved. Subsequently, to the solution was added 100 g of zinc oxide, and the mixture was stirred for 1 hour at room temperature. The solvent was removed, and the residue was dried (70° C., 24 hours) and powdered.

TEST EXAMPLE 2

Fluorine Treatment+Cation Treatment

To 300 mL of isopropyl alcohol were added 7 g of perfluoroalkyl phosphate and 3 g of tetradecyltrimethylammonium chloride and they were dissolved. Subsequently, to the solution was added 150 g of titanium dioxide, and the mixture was stirred for 1 hour at room temperature. The solvent was removed, and the residue was dried (70° C., 24 hours) and powdered.

TEST EXAMPLE 3

Metallic Soap Treatment+Cation Treatment

To 400 mL of isopropyl alcohol were added 20 g of stearic acid and 2 g of stearyltrimethylammonium chloride and they were dissolved. Subsequently, to the solution was added 200 g of zinc oxide, and the mixture was stirred for 1 hour at room temperature. The solvent was removed, and the residue was dried (70° C., 24 hours) and powdered.

TEST EXAMPLE 4

Silicone Treatment+Cation Treatment

To 300 mL of isopropyl alcohol were added 12 mL of dimethylpolysiloxane, 30 g of silica and 6 g of hexadecyltrimethylammonium chloride and they were dissolved. Subsequently, to the solution was added 150 g of titanium dioxide, and the mixture was stirred for 1 hour at room temperature. The solvent was removed, and the residue was dried (70° C., 24 hours) and powdered.

TEST EXAMPLE 5

Silane Coupling Agent Treatment

A similar treatment to Test Example 1 was carried out except that diC18dimethylammonium salt was not added.

TEST EXAMPLE 6

Fluorine Treatment

A similar treatment to Test Example 2 was carried out except that tetradecyltrimethylammonium chloride was not added.

TEST EXAMPLE 7

Metallic Soap Treatment

A similar treatment to Test Example 3 was carried out except that stearyltrimethylammonium chloride was not added.

TEST EXAMPLE 8

Silicone Treatment

A similar treatment to Test Example 4 was carried out except that hexadecyltrimethylammonium chloride was not added.

TEST EXAMPLE 9

Cation Treatment

To 200 mL of isopropyl alcohol were added 5 g of hexadecyltrimethylammonium chloride and they were dissolved. Subsequently, to the solution was added 100 g of zinc oxide, and the mixture was stirred for 1 hour at room temperature. The solvent was removed, and the residue was dried (70° C., 24 hours) and powdered.

Sunscreen cosmetic compositions of the below-described formulation were prepared using powders of the above-described Test Examples 1 to 9, and the cleansability, water resistance, and ultraviolet protection effect were tested.

| (formulation) | (% by mass) |
|---|---|
| (1) Powder of respective test examples | 15 |
| (2) Dimethylpolysiloxane | 1 |
| (3) Decamethylcyclopentasiloxane | 25 |
| (4) Trimethyl siloxy silicate | 5 |
| (5) Polyoxyethylene-methylpolysiloxane copolymer | 2 |
| (6) Isononyl isononanoate | 4 |
| (7) Dipropylene glycol | 5 |
| (8) Dipotassium glycyrrhizinate | 0.02 |
| (9) Glutathione | 1 |
| (10) Thiotaurine | 0.05 |
| (11) *Sophora angustifolia* root extract | 1 |
| (12) Paraben | appropriate amount |
| (13) Phenoxyethanol | appropriate amount |
| (14) 2-ethylhexyl-paramethoxy cinnamate | 7.5 |
| (15) Dimethyldistearylammonium hectorite | 0.5 |
| (16) Spheric alkyl polyacrylate powder | 5 |
| (17) Butylethylpropanediol | 0.5 |
| (18) Purified water | balance |

The test results are shown in Table 1.

TABLE 1

| | Cleansability | Water resistance | Ultraviolet protection effect |
|---|---|---|---|
| Test Example 1 | A | A | A |
| Test Example 2 | A | A | A |
| Test Example 3 | A | A | A |
| Test Example 4 | A | A | A |
| Test Example 5 | C | A | A |
| Test Example 6 | C | A | A |
| Test Example 7 | C | A | A |
| Test Example 8 | C | A | A |
| Test Example 9 | B | C | C |

As shown for Test Examples 5 to 8, sunscreen cosmetic compositions containing a powder generated only by hydrophobizing treatment had good water resistance, but the cleansability was poor.

In contrast, sunscreen cosmetic compositions containing a powder of Test Examples 1 to 4, namely, a modified powder of the present invention, had markedly improved cleansability because of the combination of the hydrophobizing treatment and cation treatment.

As shown for Test Example 9, sunscreen cosmetic composition containing a powder generated only by the cation treatment had good cleansability, but the water resistance and ultraviolet protection effect were poor.

Thus, it was confirmed that a powder with both water resistance and cleansability could be obtained by coating the powder surface with a hydrophobizing agent and a cationic surfactant.

EXAMPLE 2

In order to confirm that the surface is undoubtedly covered with a cationic surfactant, the cosmetics of the below-described formulation were prepared, and the cleansability, water resistance, and ultraviolet protection effect were tested.

TABLE 2

| | Blending Example 1 | Blending Example 2 | Blending Example 3 |
|---|---|---|---|
| Powder of Test Example 4 | 15 | — | — |
| Powder of Test Example 8 | — | 14 | 14 |
| Hexadecyltrimethylammonium chloride | — | 1 | — |
| Dimethylpolysiloxane | 1 | 1 | 1 |
| Decamethylcyclopentasiloxane | 25 | 25 | 25 |
| Trimethyl siloxy silicate | 5 | 5 | 5 |
| Polyoxyethylene-methylpolysiloxane copolymer | 2 | 2 | 2 |
| Cetyl octanoate | 4 | 4 | 4 |
| Dipropylene glycol | 5 | 5 | 5 |
| Dipotassium glycyrrhizinate | 0.02 | 0.02 | 0.02 |
| Glutathione | 1 | 1 | 1 |
| Thiotaurine | 0.05 | 0.05 | 0.05 |
| *Sophora angustifolia* root extract | 1 | 1 | 1 |
| Paraben | appropriate amount | appropriate amount | appropriate amount |
| Phenoxyethanol | appropriate amount | appropriate amount | appropriate amount |
| 2-ethylhexyl-paramethoxy cinnamate | 7.5 | 7.5 | 7.5 |
| Dimethyldistearylammonium hectorite | 0.5 | 0.5 | 0.5 |
| Spheric alkyl polyacrylate powder | 5 | 5 | 5 |
| Butylethylpropanediol | 0.5 | 0.5 | 0.5 |
| Purified water | balance | balance | balance |
| Cleansability | A | B | C |
| Water resistance | A | A | A |
| Ultraviolet protection effect | A | A | A |

By comparing Blending Example 2 and Blending Example 3, it was found that some improvement in cleansability could be achieved even when a cationic surfactant was added to the formulation. By comparing Blending Example 1 and Blending Example 2, however, it was found that the improvement in cleansability was more effective when a cationic surfactant was coated on the surface of the powder.

Thus, it was confirmed that the surface is undoubtedly coated with a cationic surfactant in the treated powder of the present invention and that the powder with both water resistance and cleansability could be achieved by coating the surface of the powder with both a hydrophobizing agent and a cationic surfactant.

EXAMPLE 3

The desirable amount of a coated hydrophobizing agent and the desirable amount of a coated cationic surfactant were also investigated. Cosmetic compositions containing the modified powders of Test Examples 10-1 to 10-7 (Table 3) were prepared, and the cleansability and water resistance were tested. The powder of each test example was prepared according to the preparation method of Test Example 1. The formulation of cosmetic compositions containing each powder is shown below.

| (formulation) | (% by mass) |
|---|---|
| (1) Powder of respective test examples | 15 |
| (2) Dimethylpolysiloxane | 1 |
| (3) Decamethylcyclopentasiloxane | 25 |
| (4) Trimethyl siloxy silicate | 5 |
| (5) Polyoxyethylene-methylpolysiloxane copolymer | 2 |
| (6) Isononyl isononanoate | 4 |
| (7) Dipropylene glycol | 5 |
| (8) Dipotassium glycyrrhizinate | 0.02 |
| (9) Glutathione | 1 |

-continued

| (formulation) | (% by mass) |
|---|---|
| (10) Thiotaurine | 0.05 |
| (11) *Sophora angustifolia* root extract | 1 |
| (12) Paraben | appropriate amount |
| (13) Phenoxyethanol | appropriate amount |
| (14) 2-ethylhexyl-paramethoxy cinnamate | 7.5 |
| (15) Dimethyldistearylammonium hectorite | 0.5 |
| (16) Spheric alkyl polyacrylate powder | 5 |
| (17) Butylethylpropanediol | 0.5 |
| (18) Purified water | balance |

TABLE 3

| | Test Example | | | | | | |
|---|---|---|---|---|---|---|---|
| | 10-1 | 10-2 | 10-3 | 10-4 | 10-5 | 10-6 | 10-7 |
| Composition of modified powder | | | | | | | |
| (1) Titanium dioxide | 100 g | 100 g | 100 g | 100 g | 100 g | 100 g | — |
| (2) Non-aluminum-containing titanium oxide | — | — | — | — | — | — | 100 g |
| (3) Silane coupling agent | 4.5 g | 90 g | 3 g | 6 g | 6 g | 120 g | 6 g |
| (4) Cation treatment agent | 0.5 g | 10 g | 3 g | 2 g | 12 g | 10 g | 2 g |
| (3):(4) | 9:1 | 9:1 | 1:1 | 3:1 | 1:2 | 12:1 | 3:1 |
| Cleansability | B | A | A | A | A | C | A |
| Water resistance | B | A | A | A | D | A | A |

It was confirmed that when the amount of coated hydrophobizing agent and the amount of coated cationic surfactant were 3 to 90% by mass and 0.5 to 10% by mass, respectively, relative to the self weight of the base powder, a powder with both water resistance and cleansability could be obtained.

In addition, it was confirmed that when the mass ratio of the coated hydrophobizing agent and the coated cationic surfactant was from 1:1 to 9:1, a powder with both water resistance and cleansability could be obtained.

EXAMPLE 4

The effect of coating with a hydrophobizing agent and a cationic surfactant was tested when non-aluminum-containing titanium oxide was used as the base powder.

At first, silica coated titanium oxide was obtained by coating the surface of non-aluminum-containing titanium oxide powder with silica by the method described below.

<Preparation Method of Silica Coated Titanium Oxide>

An aqueous slurry of 2 kg of non-aluminum-containing rutile-type titanium oxide (average particle size: 0.02×0.09 μm) was prepared and heated to 60° C. To the slurry, 3 L of sodium silicate aqueous solution, the concentration of which was 100 g/L as $SiO_3$, was added during the course of 1 hour. Subsequently, the temperature was raised to 90° C., and the mixture was aged for 1 hour. Then, the mixture was neutralized with 20% sulfuric acid, during the course of 30 minutes, so that the pH would be 5.5. Thus, the silica coating of the composite surface was achieved.

Next, the silica coated titanium oxide obtained by the above-described method was treated, as described below, to obtain respective modified powders.

TEST EXAMPLE 11

Silica Coated Titanium Oxide/Silane Coupling Agent Treatment+Cation Treatment

To 200 mL of isopropyl alcohol were added 6 g of octyltriethoxysilane and 2 g of C18 dimethylammonium salt, and they were dissolved. Subsequently, to the solution was added 100 g of silica coated titanium oxide (non-aluminum-containing) prepared by the above-described method, and the mixture was stirred for 1 hour at room temperature. The solvent was removed, and the residue was dried (70° C., 24 hours) and powdered.

TEST EXAMPLE 12

Silica Coated Titanium Oxide/Silane Coupling Agent Treatment

A similar treatment to Test Example 11 was carried out except that di C18 dimethylammonium salt was not added.

Sunscreen cosmetic compositions of the below-described formulation were prepared using the powders of respective test examples.

| (formulation) | (% by mass) |
|---|---|
| (1) Powder of respective test examples | 14 |
| (2) Dimethylpolysiloxane | 12 |
| (3) Isononyl isononanoate | 3 |
| (4) Heptamethyloctyltrisiloxane | 5 |
| (5) Trioctanoin | 5 |
| (6) Isopropyl sebacate | 10 |
| (7) Isostearic acid | 0.5 |
| (8) Trimethyl siloxy silicate | 5 |
| (9) Lauryl PEG-9 polydimethylsiloxyethyl dimethicone | 1.5 |
| (10) Polyoxyethylene-methylpolysiloxane copolymer | 0.5 |
| (11) Dimethyldistearylammonium hectorite | 0.3 |
| (12) 4-tert-butyl-4'-methoxybenzoylmethane | 3 |
| (13) Ethylhexyl 2-cyano-3,3-diphenyl acrylate | 5 |
| (14) Phenylbenzimidazole sulfonic acid | 2 |
| (15) Triethanolamine | 1.5 |
| (16) Glutathione | 1 |
| (17) Phenoxyethanol | appropriate amount |
| (18) Spheric alkyl polyacrylate powder | 5 |
| (19) Ethyl alcohol | 3 |
| (20) 1,3-butylene glycol | 5 |
| (21) Purified water | balance |

Sunscreen cosmetic compositions containing the powder of Test Example 11 and the powder of Test Example 12 were tested, respectively, for the cleansability, water resistance, and ultraviolet protection effect according to the test methods of Example 1. The results are shown in Table 4.

TABLE 4

| | Cleansability | Water resistance | Ultraviolet protection effect |
|---|---|---|---|
| Test Example 11 | A | A | A |
| Test Example 12 | C | A | A |

As shown for Test Example 12, the sunscreen cosmetic composition containing the powder generated only by hydrophobizing treatment had good water resistance, but the cleansability was poor.

On the other hand, the sunscreen cosmetic compositions containing the powder of Test Example 11, in which both hydrophobizing treatment and cationic surfactant treatment were carried out, were confirmed to have significantly improved cleansability as well as good water resistance.

In order to verify the ultraviolet protection effect, the absorbances of sunscreen cosmetic compositions containing the powder of Test Example 11 and the powder of Test Example 12 were measured, respectively. For the absorbance measurement, a nylon film was used as the application medium, and 2 mg of the cosmetics were applied per $cm^2$. The absorbance was measured with a spectrophotometer.

Figure 1:
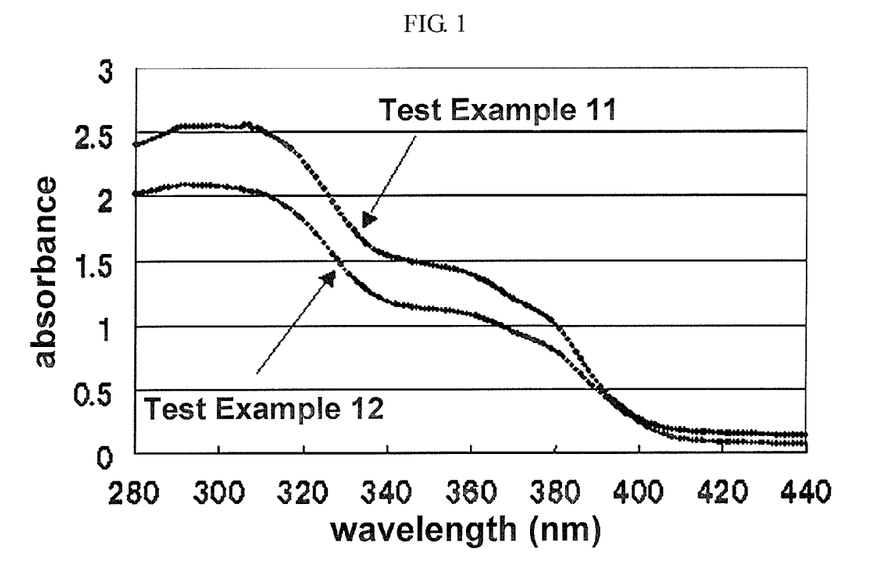
FIG. 1 shows the absorbance for the cosmetics in Test Examples 11 and 12 of the present invention.
Figure 2:
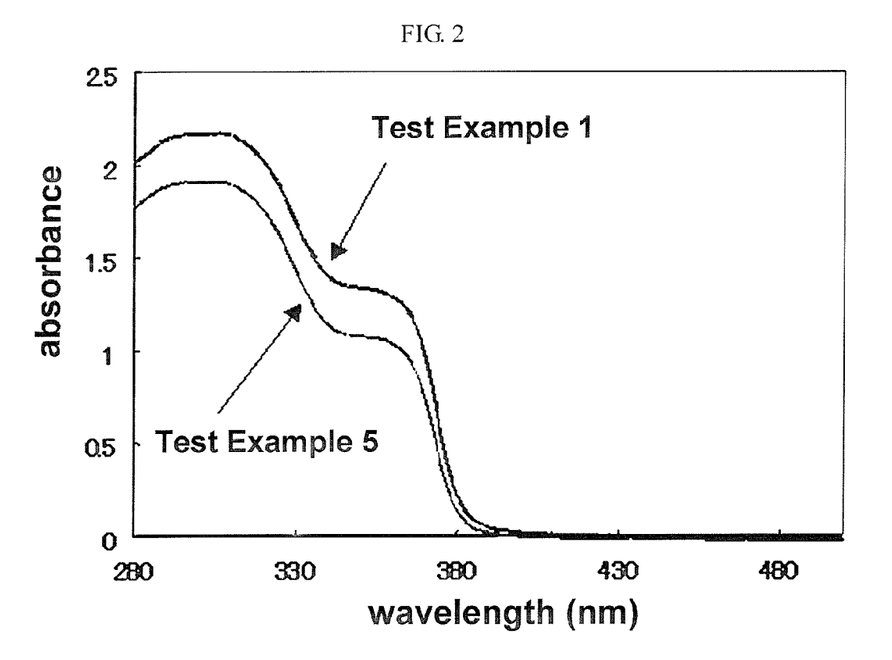
FIG. 2 shows the absorbance for the cosmetics in Test Examples 1 and 5 of the present invention.

The results of absorbance measurement for the sunscreen cosmetics of Test Examples 11 and 12 are shown in FIG 1. For comparison, the absorbances, measured by the same method, for the cosmetics of Test Examples 1 and 5 are shown in FIG 2.

For each powder, the test examples with hydrophobizing treatment and cationic surfactant treatment have high absorbance in the long wavelength region (320-400 nm) and middle wavelength region (290-320 nm); thus, the ultraviolet protection effect was better than the other test examples. On the other hand, the absorbance is significantly low in the visible region (400-700 nm); thus, it was confirmed that the transparency was maintained. This is probably due to the improved powder dispersion in the composition because of the hydrophobizing treatment and cationic surfactant treatment.

In the case of the powder with non-aluminum-containing titanium oxide, dibenzoylmethane group ultraviolet light absorbers, which have been incompatible in the past, can be stably blended in. As a result, the composition with the wide ultraviolet protection in both UVA and UVB regions and with the overall high effect could be obtained.

Next, a sample of each test example was approximately half-filled in a 50 mL glass tube, the tube was placed on a roller rotating at 40 rpm/min, and the viscosity stability after 4 hours was evaluated (rolling stability test).

The results are shown in Table 5.

TABLE 5

|  | Test Example | |
| --- | --- | --- |
|  | 11 | 12 |
| Viscosity (mPa · s) | 850 | 3730 |
| Stability | ◯ | X |

As seen in the above-described results, the stability deterioration with time, due to powder aggregation, could be remedied by the hydrophobizing treatment and cationic surfactant treatment of powder.

Examples of the cosmetic composition of the present invention are described below. However, the present invention is not limited by these examples.

In all examples, the cosmetic composition was prepared by the normal method.

EXAMPLE 5

<Powder Foundation>

| (formulation) | (% by mass) |
| --- | --- |
| (1) Alpha-olefin oligomer | 3 |
| (2) Dimethylpolysiloxane | 8 |

-continued

| (formulation) | (% by mass) |
| --- | --- |
| (3) Methylhydrogenpolysiloxane | 0.5 |
| (4) Sorbitan sesquiisostearate | 1 |
| (5) Calcium hydrogen phosphate | 3 |
| (6) Silane coupling agent + cation treated yellow iron oxide (cation: dihexadecyldimethylammonium salt) | 2 |
| (7) Silane coupling agent + cation treated red iron oxide (cation: distearyldimethylammonium salt) | 1 |
| (8) Silane coupling agent + cation treated black iron oxide (cation: ditetradecyldimethylammonium salt) | appropriate amount |
| (9) Silane coupling agent + cation treated titanium oxide (cation: didodecyldimethylammonium salt) | 10 |
| (10) Silane coupling agent + cation treated talc (cation: stearyltrimethylammonium chloride) | 5 |
| (11) Low temperature fired zinc oxide | 5 |
| (12) Barium sulfate | 2 |
| (13) Fired sericite | 10 |
| (14) Bronze mica | balance |
| (15) Spheric polymethylsilsesquioxane powder | 3 |
| (16) Cross-linked silicone-networked silicone block copolymer powder | 5 |
| (17) DL-alpha-tocopherol acetate | 0.1 |
| (18) D-delta-tocopherol | 0.1 |
| (19) Thiotaurine | 0.1 |
| (20) Para-hydroxybenzoate ester | appropriate amount |
| (21) 2-ethylhexyl-paramethoxy cinnamate | 3 |
| (22) Silicic anhydride | 1 |
| (23) Titanium oxide | 2 |

EXAMPLE 6

<Emulsion Foundation>

| (formulation) | (% by mass) |
| --- | --- |
| (1) Dimethylpolysiloxane | 3 |
| (2) Decamethylcyclopentasiloxane | 10 |
| (3) Polyoxyethylene-methylpolysiloxane copolymer | 3 |
| (4) Dodecamethylcyclohexasiloxane | 5 |
| (5) Glycerin | 4 |
| (6) 1,3-butylene glycol | 5 |
| (7) Palmitic acid | 0.5 |
| (8) Distearyldimethylammonium chloride | 0.2 |
| (9) Silane coupling agent + cation treated talc (cation: dihexadecyldimethylammonium salt) | 2 |
| (10) Cross-linked silicone powder (TOREFILL E-506 (treadmark)) | 0.1 |
| (11) Red iron oxide coated titanated mica | 0.5 |
| (12) N-lauroyl-L-lysine | 2 |
| (13) Monosodium L-glutamate | 2 |
| (14) Tocopherol acetate | 0.1 |
| (15) Delta-tocopherol | 0.1 |
| (16) Para-hydroxybenzoate ester | appropriate amount |
| (17) Phenoxyethanol | 0.2 |
| (18) Spheric nylon powder | 1 |
| (19) Spheric alkyl polyacrylate powder | 3 |
| (20) Melilot extract | 2 |
| (21) Purified water | balance |
| (22) Silane coupling agent + cation treated talc (cation: dihexadecyldimethylammonium salt) | 3 |
| (23) Silane coupling agent + cation treated titanium dioxide (cation: distearyldimethylammonium salt) | 15 |
| (24) Silane coupling agent + cation treated yellow iron oxide (cation: ditetradecyldimethylammonium salt) | 3 |

EXAMPLE 7

<Eyeliner>

| (formulation) | (% by mass) |
|---|---|
| (1) Decamethylcyclopentasiloxane | 30 |
| (2) Polyoxyethylene-methylpolysiloxane copolymer | 3 |
| (3) 1,3-butylene glycol | 2 |
| (4) Isostearic acid | 1 |
| (5) Di-(phytosteryl/2-octyldodecyl) N-lauroyl-L-glutamate | 0.1 |
| (6) Sorbitan sesquiisostearate | 15 |
| (7) Silane coupling agent + cation treated black iron oxide (cation: hexadecyltrimethylammonium chloride) | 5 |
| (8) Silane coupling agent + cation treated talc (cation: tetradecyltrimethylammonium chloride) | 3 |
| (9) Titanated mica (pearl agent) | 5 |
| (10) Sodium hydroxide | 0.05 |
| (11) Sodium chloride | 0.2 |
| (12) Glycine | 0.3 |
| (13) DL-alpha-tocopherol acetate | 0.05 |
| (14) Para-hydroxybenzoate ester | appropriate amount |
| (15) Phenoxyethanol | appropriate amount |
| (16) Dimethyldistearylammonium hectorite | 1.5 |
| (17) Trimethyl siloxy silicate | 10 |
| (18) Purified water | balance |

EXAMPLE 8

<Mascara>

| (formulation) | (% by mass) |
|---|---|
| (1) Decamethylcyclopentasiloxane | 20 |
| (2) Polyoxyethylene-methylpolysiloxane copolymer | 2 |
| (3) Methylphenylpolysiloxane | 2 |
| (4) 1,3-butylene glycol | 2 |
| (5) Macadamia nut oil | 0.1 |
| (6) Oleic acid | 1 |
| (7) Sorbitan sesquiisostearate | 2 |
| (8) Silane coupling agent + cation treated talc (cation: dodecyltrimethylammonium chloride) | 5 |
| (9) Silane coupling agent + cation-treated titanated mica (pearl agent) (cation: distearyldimethylammonium salt) | 17 |
| (10) Sodium hydroxide | 0.1 |
| (11) Sodium chloride | 0.2 |
| (12) Glycine | 0.3 |
| (13) D-delta-tocopherol | appropriate amount |
| (14) Para-hydroxybenzoate ester | appropriate amount |
| (15) Phenoxyethanol | appropriate amount |
| (16) Dimethyldistearylammonium hectorite | 3 |
| (17) Trimethyl siloxy silicate | 10 |
| (18) Purified water | balance |

EXAMPLE 9

| (formulation) | (% by mass) |
|---|---|
| (1) Dimethylpolysiloxane 6 mPa·s | 2 |
| (2) Decamethylcyclopentasiloxane | 40 |
| (3) Polyoxyethylene-methylpolysiloxane copolymer | 2 |
| (4) 1,3-butylene glycol | 5 |
| (5) Squalane | 0.5 |
| (6) Isostearic acid | 0.5 |
| (7) Silane coupling agent + cation-reated fine zinc oxide particle 50 nm (cation: dihexadecyldimethylammonium salt) | 0.5 |
| (8) Silane coupling agent + cation-treated fine titanium oxide particle 30 nm (cation: ditetradecyldimethylammonium salt) | 15 |
| (9) Dipotassium glycyrrhizinate | 0.5 |
| (10) DL-alpha-tocopherol acetate | 0.1 |
| (11) D-delta-tocopherol | 0.1 |
| (12) Para-hydroxybenzoate ester | appropriate amount |
| (13) Phenoxyethanol | appropriate amount |
| (14) Edentate trisodium | appropriate amount |
| (15) Silane coupling agent + cation treated yellow iron oxide (cation: didodecyldimethylammonium salt) | 0.4 |
| (16) Dimethyldistearylammonium hectorite | 0.3 |
| (17) Purified water | balance |
| (18) Trimethyl siloxy silicate | 1.5 |
| (19) Spheric polyethylene powder | 5 |
| (20) Aluminum oxide | 0.2 |

EXAMPLE 10

<Lipstick>

| (formulation) | (% by mass) |
|---|---|
| (1) Microcrystalline wax | 2 |
| (2) Ceresin | 11 |
| (3) Liquid lanolin | 2 |
| (4) Squalane | 1 |
| (5) Macadamia nut fatty acid cholesteryl | 8 |
| (6) Diisostearyl malate | 10 |
| (7) Glyceryl diisostearate | 5 |
| (8) Glyceryl tri-2-ethylhexanoate | 30 |
| (9) Isostearyl oxystearate | 10 |
| (10) Silane coupling agent + cation treated pigment (cation: dihexadecyldimethylammonium salt) | 4 |
| (11) Barium sulfate | 4 |
| (12) Red iron oxide coated titanated mica | 0.1 |
| (13) Phytosterol | 0.1 |
| (14) Heavy liquid isoparaffin | 10 |
| (15) Dye | appropriate amount |
| (16) Perfume | appropriate amount |

What is claimed is:

1. A modified powder that is obtainable by coating the surface of a base powder with octyltriethoxysilane and a cationic surfactant.

2. The modified powder of claim 1, wherein the amount of coated octyltriethoxysilane and the amount of coated cationic surfactant are 3 to 90% by mass and 0.5 to 10% by mass, respectively, relative to the weight of the base powder.

3. The modified powder of claim 1, wherein the mass ratio of the coated octyltriethoxysilane and the coated cationic surfactant is from 1:1 to 9:1.

4. The modified powder of claim 1, wherein the base powder has an ultraviolet light scattering effect.

5. A cosmetic composition comprising the modified powder of claim 1.

6. The cosmetic composition according to claim 5, wherein the blended amount of the modified powder is from 0.5 to 100% by mass.

7. A sunscreen cosmetic composition comprising the modified powder according to claim 4.

8. The sunscreen cosmetic composition according to claim 7, wherein the base powder is one or more selected from the group consisting of titanium oxide, zinc oxide, iron oxide, cerium oxide, bismuth oxide, zirconium oxide, chromium oxide, and tungstic acid.

9. The sunscreen cosmetic composition of claim 7, wherein the sunscreen cosmetic composition comprises 1 to 40% by mass of the modified powder.

10. The modified powder of claim 1, wherein the base powder is one or more selected from the group consisting of titanium oxide, black titanium oxide, Prussian blue, ultramarine, red iron oxide, yellow iron oxide, black iron oxide, zinc oxide, aluminum oxide, silicon dioxide, magnesium oxide, zirconium oxide, magnesium carbonate, calcium carbonate, chromium oxide, tungstic acid, chromium hydroxide, carbon black, aluminum silicate, magnesium silicate, magnesium aluminum silicate, mica, synthetic mica, synthetic sericite, sericite, talc, kaolin, silicon carbide, barium sulfate, bentonite, smectite, boron nitride, bismuth oxychloride, titanated mica, iron oxide coated mica, iron oxide-coated titanated mica, organic pigment-treated titanated mica, aluminum; nylon, polymethyl methacrylate, acrylonitrile-methacrylic acid copolymer, vinylidene chloride-methacrylic acid copolymer, polyethylene, polystyrene, organopolysiloxane elastomer, polymethylsilsesquioxane, wool, silk, crystalline cellulose, and N-acyllysine; tar pigments, lake pigments, titanium oxide particle-coated titanated mica, zinc oxide particle-coated titanated mica, barium sulfate-coated titanated mica, silicon dioxide-containing titanium oxide, and silicon dioxide-containing zinc oxide.

11. The modified powder of claim 1, wherein the cationic surfactant is selected from the group consisting of stearyltrimethylammonium chloride, hexadecyltrimethylammonium chloride, tetradecyltrimethylammonium chloride, lauryltrimethylammonium chloride, C12 monohydroxyalkylether cation, dihydroxyalkylether cation, cocodiamidopropyl cation, cocodicarboxyethyl cation, C16 dicarboxyethyl cation, C18 dicarboxyethyl cation, POP(15) diethylmethyl cation, POP (25) diethylmethyl cation, POP(40) diethylmethyl cation, C12 diamidopropylmethylamine, C14 diamidopropylmethylamine, C16 diamidopropylmethylamine, C18 diamidopropylmethylamine, iso-C18 diamidopropylmethylamine, di-C18 propyldimethyl cation, hydroxypropyl-bis-lauryl cation, hydroxypropyl-bis-stearyl cation, hydroxypropyl-bis-laurylamide cation, hydroxypropyl-bis-stearylamide cation, C18 monohydroxyalkylether cation, bis-C18 hydroxyalkylether cation, C22 trimethylammonium bromide, C22 propyldimethylamine, quaternium-91, C22 trimethylammonium methosulfate, dicocoylamidoethylethylhydroxy cation, di C18 amidoethylethylhydroxy cation, di C16 amidoethylethylhydroxy cation, di C18 dimethylammonium salt, C18 dimethylbenzylammonium salt, perfluorotrimethylammonium salt, diacylamidoethylethylhydroxy cation, and combinations thereof.

12. A modified powder comprising:
(a) a base powder selected from the group consisting of titanium oxide, black titanium oxide, Prussian blue, ultramarine, red iron oxide, yellow iron oxide, black iron oxide, zinc oxide, aluminum oxide, silicon dioxide, magnesium oxide, zirconium oxide, magnesium carbonate, calcium carbonate, chromium oxide, tungstic acid, chromium hydroxide, carbon black, aluminum silicate, magnesium silicate, magnesium aluminum silicate, mica, synthetic mica, synthetic sericite, sericite, talc, kaolin, silicon carbide, barium sulfate, bentonite, smectite, boron nitride, bismuth oxychloride, titanated mica, iron oxide coated mica, iron oxide-coated titanated mica, organic pigment-treated titanated mica, aluminum; nylon, polymethyl methacrylate, acrylonitrile-methacrylic acid copolymer, vinylidene chloride-methacrylic acid copolymer, polyethylene, polystyrene, organopolysiloxane elastomer, polymethylsilsesquioxane, wool, silk, crystalline cellulose, and N-acyllysine; tar pigments, lake pigments, titanium oxide particle-coated titanated mica, zinc oxide particle-coated titanated mica, barium sulfate-coated titanated mica, silicon dioxide-containing titanium oxide, silicon dioxide-containing zinc oxide, and combinations thereof;
(b) octyltriethoxysilane, and
(c) a cationic surfactant selected from the group consisting of stearyltrimethylammonium chloride, hexadecyltrimethylammonium chloride, tetradecyltrimethylammonium chloride, lauryltrimethylammonium chloride, C12 monohydroxyalkylether cation, dihydroxyalkylether cation, cocodiamidopropyl cation, cocodicarboxyethyl cation, C16 dicarboxyethyl cation, C18 dicarboxyethyl cation, POP(15) diethylmethyl cation, POP(25) diethylmethyl cation, POP(40) diethylmethyl cation, C12 diamidopropylmethylamine, C14 diamidopropylmethylamine, C16 diamidopropylmethylamine, C18 diamidopropylmethylamine, iso-C18 diamidopropylmethylamine, di-C18 propyldimethyl cation, hydroxypropyl-bis-lauryl cation, hydroxypropyl-bis-stearyl cation, hydroxypropyl-bis-laurylamide cation, hydroxypropyl-bis-stearylamide cation, C18 monohydroxyalkylether cation, bis-C18 hydroxyalkylether cation, C22 trimethylammonium bromide, C22 propyldimethylamine, quaternium-91, C22 trimethylammonium methosulfate, dicocoylamidoethylethylhydroxy cation, di C18 amidoethylethylhydroxy cation, di C16 amidoethylethylhydroxy cation, di C18 dimethylammonium salt, C18 dimethylbenzylammonium salt, perfluorotrimethylammonium salt, diacylamidoethylethylhydroxy cation, and combinations thereof.

13. The modified powder of claim 12, wherein the amount of coated octyltriethoxysilane and the amount of coated cationic surfactant are 3 to 90% by mass and 0.5 to 10% by mass, respectively, relative to the weight of the base powder.

14. The modified powder of claim 12, wherein the mass ratio of the coated octyltriethoxysilane and the coated cationic surfactant is about 1:1 to 9:1.

15. A sunscreen composition comprising the modified powder of claim 12.

16. The sunscreen composition of claim 15, further comprising an ultraviolet light absorber selected from the group consisting of p-aminobenzoic acid (PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, homomenthyl N-acetylanthranilate, amyl salicylate, menthyl salicylate, homomenthyl salicylate, octyl salicylate, phenyl salicylate, benzyl salicylate, p-isopropanolphenyl salicylate, octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-di-parametoxy cinnamate, 2,4-dihydroxybenzophenone, 2,2'-dihydroxy-4-methoxybenzophenone, 2,2'-dihydroxy-4,4'- dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, 3-(4'-methylbenzylidene)-d,1-camphor and 3-benzylidene-d,1-camphor; 2-phenyl-5-methylbenzoxazol; 2,2'-hydroxy-5-methylphenylbenzotriazol, 2-(2'-hydroxy-5'-t-octylphenyl)benzotriazol, and 2-(2'-hydroxy-5'-methylphenylbenzotriazol; dibenzalazine; dianisoylmethane; 4-methoxy-4'-t-butyldibenzoylmethane; and 5-(3,3-dimethyl-2-norbornylidene)-3-pentane-2-one and dimorpholinopyridazinone.

17. A modified powder comprising:
  (a) a base powder selected from the group consisting of titanium oxide, zinc oxide, red iron oxide, yellow iron oxide, black iron oxide, cerium oxide, bismuth oxide, zirconium oxide, chromium oxide, and tungstic acid
  (b) octyltriethoxysilane, and,
  (c) a cationic surfactant selected from the group consisting of distearyldimethylammonium salt, dihexadecyldimethylammonium salt, ditetradecyldimethylammonium salt, didodecyldimethylammonium salt, stearyltrimethylammonium chloride, hexadecyltrimethylammonium chloride, tetradecyltrimethylammonium chloride, dodecyltrimethylammonium chloride, dialkyl substituted derivatives of the foregoing, and combinations thereof.

18. The modified powder of claim 12 comprising ultraviolet light absorbers selected from the group consisting of benzoic acid family ultraviolet light absorbers, anthranilic acid family ultraviolet light absorbers, salicylic acid family ultraviolet light absorbers, cinnamic acid family ultraviolet light absorbers, benzophenone family ultraviolet light absorbers, and combinations thereof.

19. The modified powder of claim 18, wherein the ultraviolet light absorber is selected from the group consisting of p-aminobenzoic acid (PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, homomenthyl N-acetylanthranilate, amyl salicylate, menthyl salicylate, homomenthyl salicylate, octyl salicylate, phenyl salicylate, benzyl salicylate, p-isopropanolphenyl salicylate, octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, 3-(4'-methylbenzylidene)-d, 1-camphor and 3-benzylidene-d, 1-camphor; 2-phenyl-5-methylbenzoxazol; 2,2'-hydroxy-5-methylphenylbenzotriazol, 2-(2'-hydroxy-5'-t-octylphenyl) benzotriazol, and 2-(2'-hydroxy-5'-methylphenylbenzotriazol; dibenzalazine; dianisoylmethane; 4-methoxy-4'-t-butyldibenzoylmethane; and 5-(3,3-dimethyl-2-norbornylidene)-3-pentane-2-one and dimorpholinopyridazinone.

* * * * *